__US005772731A__

United States Patent [19]

Harrison

[11] Patent Number: 5,772,731
[45] Date of Patent: Jun. 30, 1998

[54] TREATMENT OF LIQUORS

[75] Inventor: Stephen B. Harrison, London, England

[73] Assignee: The BOC Group plc, Windlesham, England

[21] Appl. No.: 801,371

[22] Filed: Feb. 19, 1997

[30] Foreign Application Priority Data

Feb. 22, 1996 [GB] United Kingdom ............... 9603747

[51] Int. Cl.$^6$ .................................................. B01D 19/00
[52] U.S. Cl. ........................... 95/8; 95/9; 95/12; 95/169; 95/170; 95/258; 95/263; 95/265; 261/DIG. 19; 261/DIG. 75
[58] Field of Search .............................. 95/159, 165, 166, 95/169–171, 258, 263, 265, 8, 9, 12, 18; 261/DIG. 19, DIG. 75

[56] References Cited

U.S. PATENT DOCUMENTS

| | | | |
|---|---|---|---|
| 3,710,549 | 1/1973 | Nichols et al. | 261/DIG. 75 |
| 4,207,180 | 6/1980 | Chang | 261/DIG. 75 |
| 4,259,360 | 3/1981 | Venetucci et al. | 95/265 X |
| 4,290,979 | 9/1981 | Sugiura | 261/DIG. 75 |
| 4,308,138 | 12/1981 | Woltman | 261/DIG. 75 |
| 4,483,826 | 11/1984 | Louthan | 261/DIG. 75 |
| 4,927,433 | 5/1990 | Wieland et al. | 95/258 X |
| 5,316,682 | 5/1994 | Keyser et al. | 261/DIG. 75 |
| 5,431,861 | 7/1995 | Nagahiro et al. | 261/DIG. 75 |
| 5,520,856 | 5/1996 | Garrett et al. | 261/DIG. 75 |
| 5,632,932 | 5/1997 | Harris et al. | 261/DIG. 75 |
| 5,674,433 | 10/1997 | Semmens et al. | 261/DIG. 75 |

FOREIGN PATENT DOCUMENTS

| | | | |
|---|---|---|---|
| 2646863 | 4/1978 | Germany | 95/169 |
| 58-025520 | 5/1983 | Japan | 95/169 |

*Primary Examiner*—Robert Spitzer
*Attorney, Agent, or Firm*—R. Hain Swope; Salvatore P. Pace

[57] ABSTRACT

A process of removing carbon dioxide from a liquor in a vessel comprises the step of continuously passing a portion of the liquor into a sidestream and introducing discrete bubbles of between 0.005 mm and 1.0 mm diameter of nitrogen rich gas into the liquor before returning it to the vessel in which the nitrogen acts to adsorb carbon dioxide from the liquor and is then expelled from the liquor as an off-gas. The process also includes introducing a gas to be dissolved in the liquor into the sidestream as discrete bubbles having a diameter of between 0.005 mm and 1.0 mm.

16 Claims, 4 Drawing Sheets

TREATMENT OF LIQUORS

The present invention relates to a process and apparatus for the treatment of liquors in a bio-reactor or the like and relates particularly, but not exclusively, to such a process for removing carbon dioxide and adding oxygen.

BACKGROUND OF THE INVENTION

Presently known bio-reactors often employ arrangements where a portion of the liquor is continuously withdrawn into a sidestream and is oxygenated by introducing bubbles of oxygen into the liquor before returning it to the reactor where the oxygen helps fuel the bio-reaction taking place therein. The sidestream flow is usually pumped and often includes a venturi device, well known to those skilled in the art, having a throat at which the oxygen is injected so as to form a plurality of discrete bubbles. Such bio-reactors often employ an air and/or inert gas injection system which injects a large volume of gas into the main body of the reactor and creates a plurality of comparatively large diameter bubbles (3–5 mm) which pass upwardly through the liquor stripping carbon dioxide therefrom as they rise to the surface. Often, the air and/or inert gas is introduced via a large and somewhat expensive diffuser manifold situated at the bottom of the reactor and provided with a large number of outlet nozzles, each of which produces a stream of comparatively large diameter bubbles for release into the liquor and is prone to fouling or blockage by biomass or other suspended solids. Once the inert gas/carbon dioxide bubbles have risen to the surface, the resulting large volume of gas mixture is typically removed and treated before release to atmosphere. This is even more necessary when reaction releases gases which are environmentally undesirable or hazardous to health, such as volatile organic compounds (VOCs).

It is an object of the present invention to provide a method and apparatus for the treatment of liquors in a bio-reactor which reduces and possibly eliminates the problems associated with the above-mentioned arrangements.

SUMMARY OF THE INVENTION

The present invention provides a process for the treatment of a liquor in a vessel by the removal of an undesired gas therefrom, wherein a portion of the liquor is continuously passed into a sidestream and a nitrogen rich gas is introduced into the sidestream in a manner which forms discrete and separate bubbles of between 0.005 mm and 1.0 mm diameter and said portion of liquor is continuously returned to the vessel wherein the nitrogen acts to adsorb the undesired gas from the liquor and is then expelled from the liquor as an off-gas. The subject process further comprises introducing a gas to dissolve in the liquor, also in the form of discrete and separate bubbles.

DETAILED DESCRIPTION OF THE INVENTION

In accordance with the present invention, the nitrogen rich gas as well as the gas to be dissolved into the liquor to be treated are introduced into the sidestream in a manner which forms discrete and separate bubbles of between 0.005 mm and 1.0 mm diameter. Preferably, the gas is introduced in a manner such that the bubbles are between 0.025 mm and 0.5 mm in diameter. Most preferably, the bubbles are about 0.2 mm in diameter as such size represents the best compromise between efficiency and cost. The fine bubbles are formed by methods well known to those skilled in the art such as passing the liquid through the high shearing force of a venturi in the sidestream as will be described below, or introducing the gas through an appropriate nozzle. The use of such a nozzle would typically be limited to treating liquids in which there is a tendency for the gas to coalesce.

The undesired gas to be removed from the liquid in accordance with the present invention is carbon dioxide. The nitrogen-rich gas can be air, but preferably is substantially pure nitrogen. The gas to be dissolved in the liquor is preferably an oxygen-rich gas, more preferably, substantially pure oxygen.

Advantageously, the process includes the step of monitoring the pH of the liquor and adjusting the supply rate of nitrogen-rich gas and oxygen-rich gas accordingly. The supply of oxygen-rich gas is likewise adjusted by monitoring the dissolved oxygen concentration in the liquor. Those skilled in the art will appreciate that conventional apparatus can be utilized to accomplish these results.

Advantageously, the process includes the step of heating the liquor within the bio-reactor so as to maintain it within a desired operating temperature, thereby maximizing stripping efficiency. Conveniently, the heating step is conduced by load managing a plurality of bio-reactors operated adjacent to each other as will be explained below. Efficiency of the overall process is enhanced by the use of low-grade waste heat from another process, if available.

Preferably, the sidestream includes a venturi having a throat and both the nitrogen-rich gas and the gas to be dissolved in the liquor are injected into the sidestream at the throat or upstream thereof. Advantageously, the sidestream is returned to the bio-reactor at or near to the bottom thereof.

Figure 1:
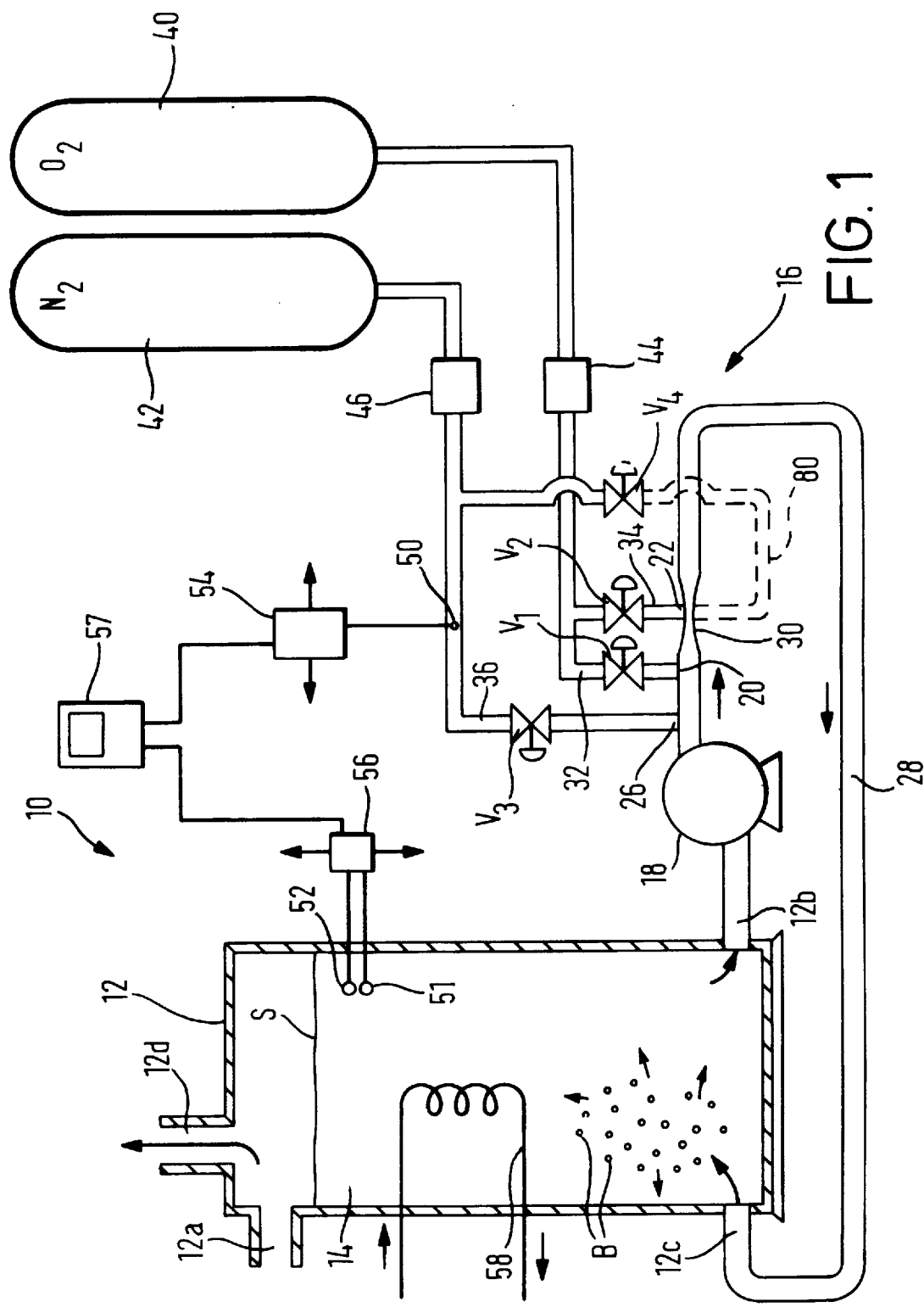
FIG. 1 is a diagrammatic representation of a bio-reactor and sidestream injection system of the present invention.
Figure 2:
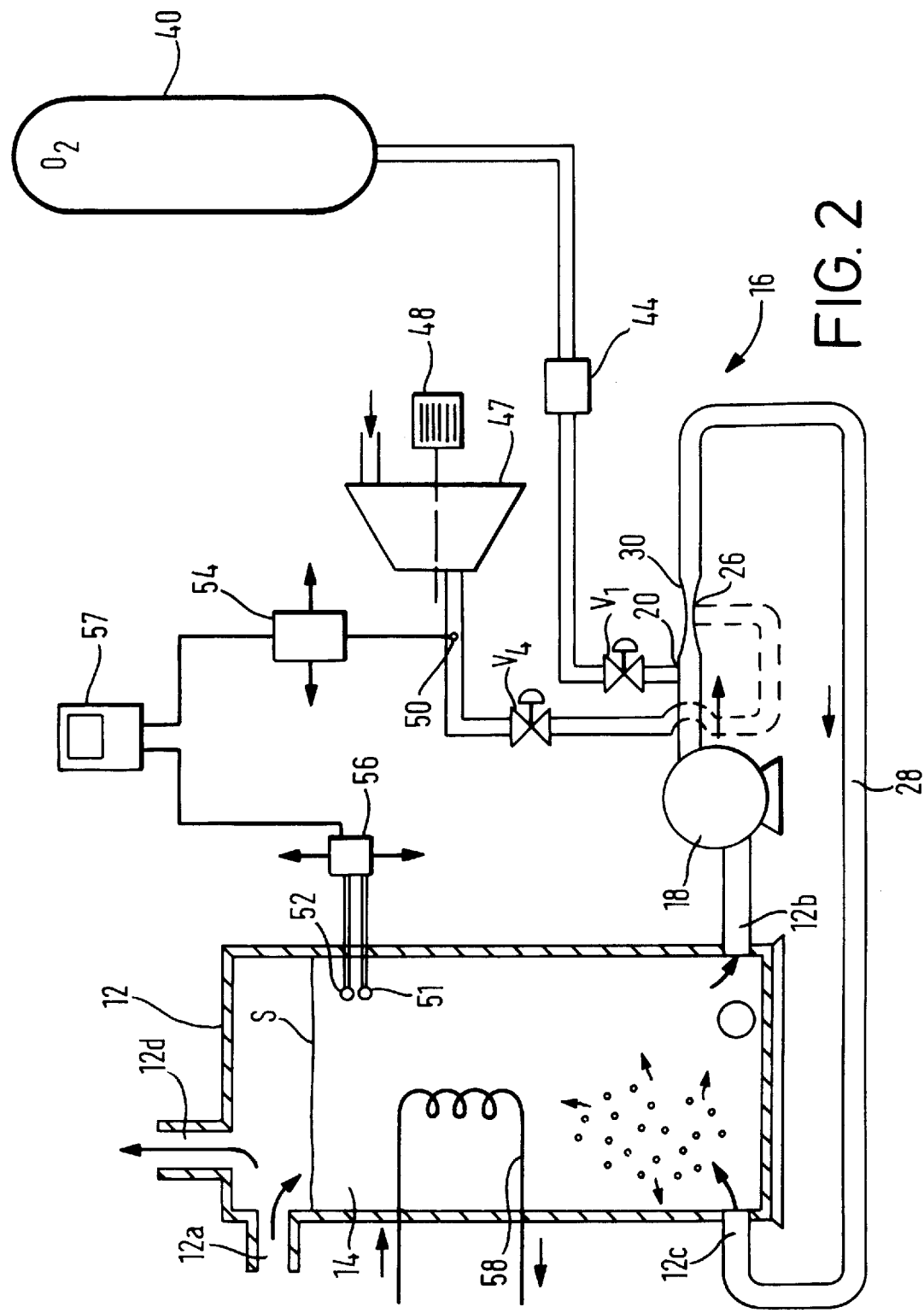
FIG. 2 illustrates an alternative form of the subject apparatus.
Figure 3:
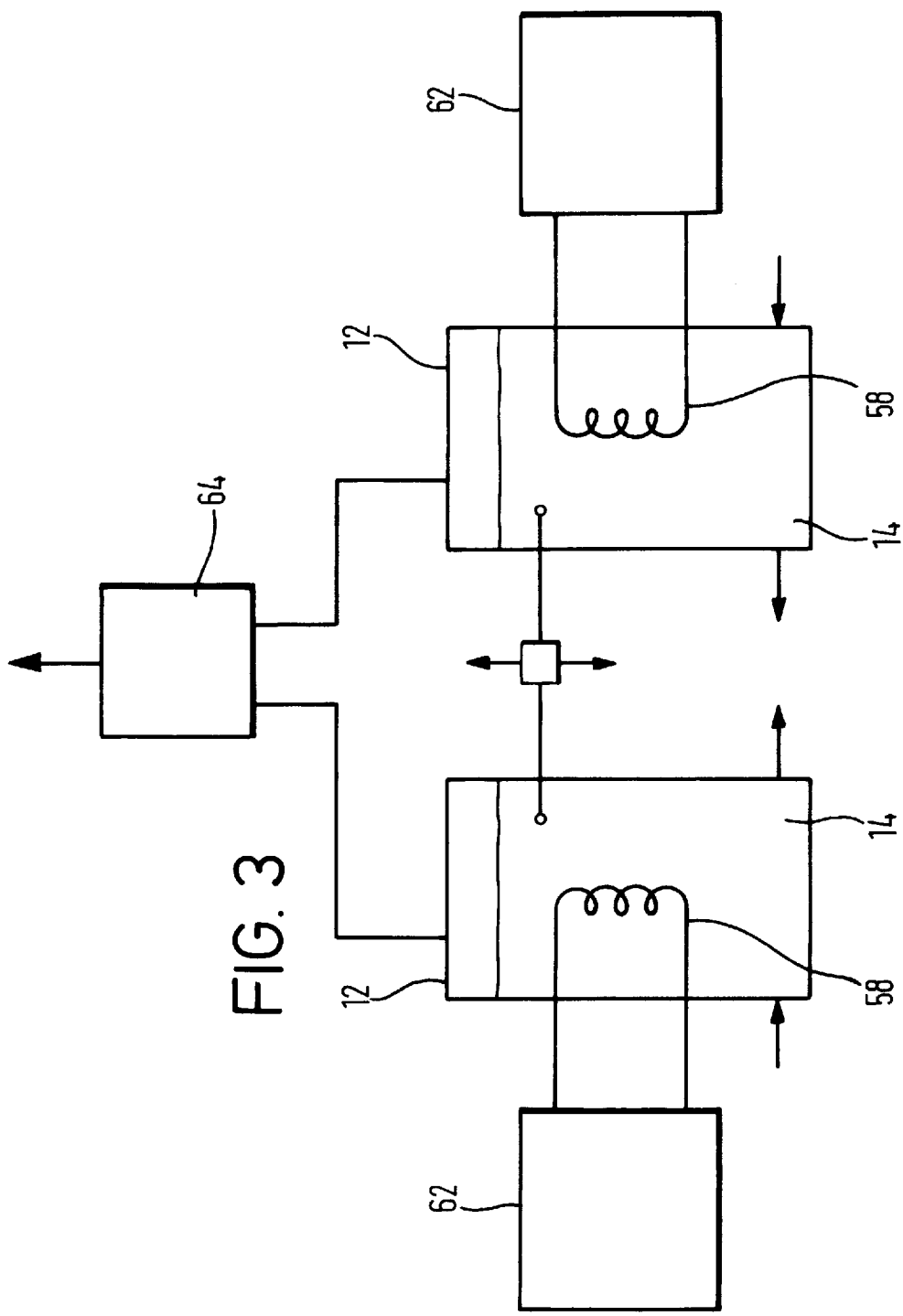
FIG. 3 is a schematic representation of a bio-reactor arrangement and includes peripheral apparatus not shown in FIGS. 1 or 2.

Referring now to the drawings, in FIGS. 1 to 3, an apparatus 10 includes a bio-reactor 12 for the treatment of a liquor 14 and a sidestream nitrogen/oxygen injection system shown generally at 16. The sidestream injection system 16 includes a pump 18 for withdrawing liquor from the reactor and various injection points 20, 22 and 26 through which one or other or both of oxygen and nitrogen are injected into the liquor. A return pipe 28 acts to return the treated liquor to the bio-reactor so that the bubbles disperse into the bulk of liquor situated therein. The sidestream system 16 may include a venturi device 30, the operation of which will be described in detail later herein. A first oxygen injection point 20 is positioned downstream of pump 18 but upstream of any venturi device 30, while a second or alternative injection point 22 comprises the throat of the venturi itself. The nitrogen is injected at point 26 downstream of pump 18 and upstream of the oxygen injection point or points 20, 22. Valves $V_1$ to $V_3$ are employed in association with supply pipes 32, 34 and 36 for allowing or inhibiting the flow of oxygen and/or nitrogen rich gas in a controlled manner described in detail later herein. While it will be appreciated that the oxygen and nitrogen rich gas may come from any one of a number of sources, it has been found that liquid storage tanks 40, 42 and associated vaporizers 44, 46 are particularly convenient. FIG. 2 however illustrates an alternative arrangement in which the source of nitrogen rich gas comprises natural air which is first compressed by compressor 47 driven by motor 48. In such an arrangement, the compressor power requirements can be kept to a minimum by injecting the nitrogen rich gas at the throat of the venturi.

Further features of the above apparatus include a nitrogen flow monitor 50 for monitoring the supply rate of nitrogen to the sidestream and a pH monitor 52 for monitoring the pH of the liquor in the bio-reactor vessel itself. In addition to this, monitoring means 51 may be provided to monitor the dissolved oxygen concentration in the liquor. Each of these monitors is operably linked to analytical controller devices shown schematically at 54 and 56, respectively, and control box 57, the operation of which will also be described in detail later herein. Preferably, the apparatus includes some form of heating means 58 for heating the liquor 14 in the bio-reactor, thereby promoting better carbon dioxide stripping. In one particularly simple arrangement, best seen in FIG. 3, the heating means 58 comprises a heat exchanger positioned within the bio-reactor 12 through which hot heat exchanging fluid may be circulated. Such fluid may be generated specifically for the purpose of heating the liquor or may comprise excess or waste heat from a nearby industrial process shown schematically at 62. Alternatively, where two or more bio-reactors 12 are operated in close proximity to each other, heating may be achieved by "load managing" the bio-reactors, i.e., diverting all or some of the feed flow from one or more of the reactors to another reactor thereby maintaining a higher temperature in the one or more reactors and, hence, promoting more efficient stripping therein. A further feature of the present invention comprises an optional off-gas scrubber shown schematically at 64 in FIG. 3 for the removal of any undesirable corrosive or toxic elements such as, for example, halogenated hydrocarbons before the escaping gas is released to atmosphere. Such devices are standard in the art and are the therefore not described herein.

Figure 4:
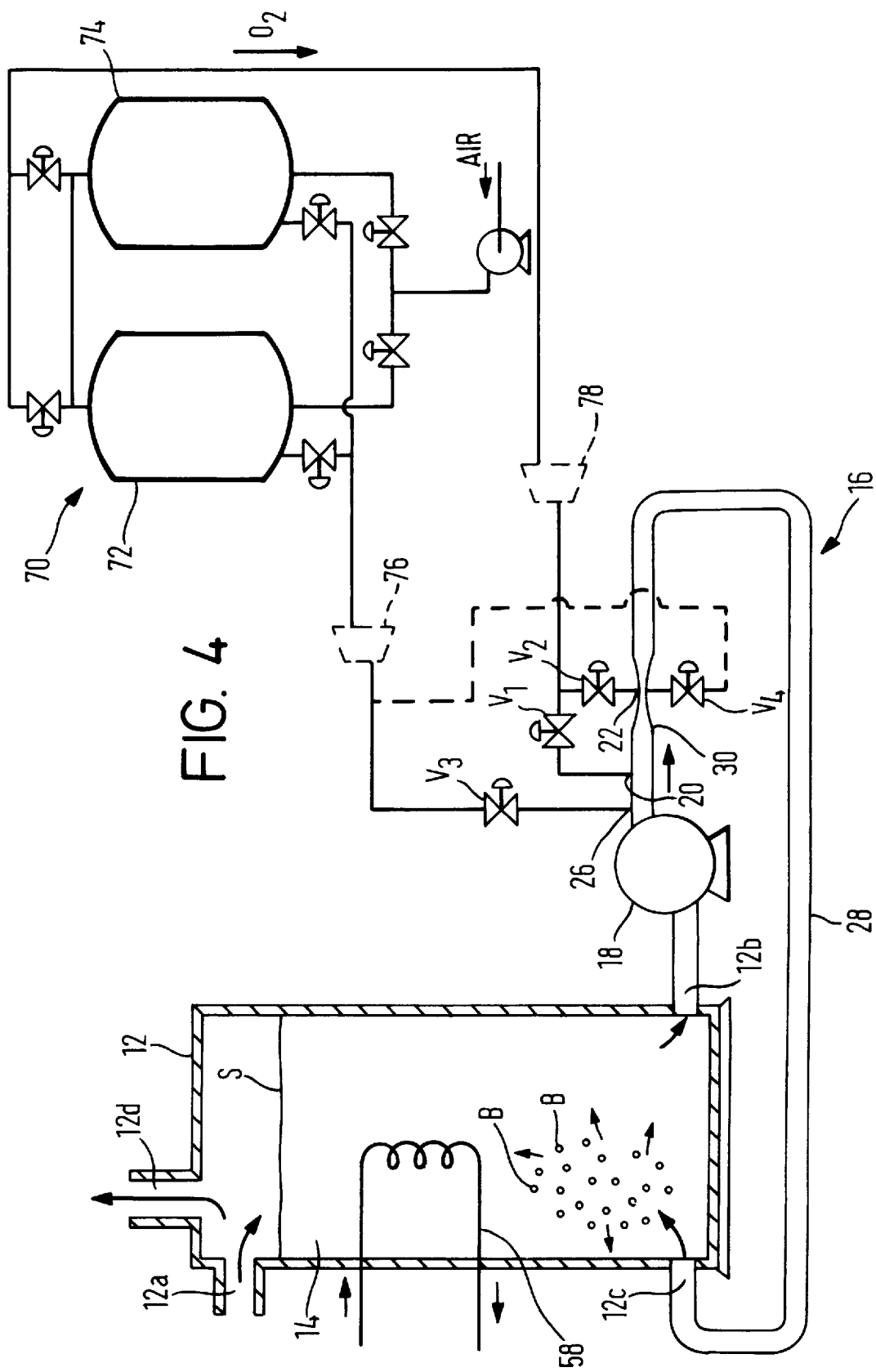
FIG. 4 illustrates the present invention when coupled to a PSA air separation apparatus.

In a further embodiment, shown in FIG. 4, the oxygen/nitrogen supply system is simplified by the utilization of an air separation device 70 of the pressure swing adsorption (PSA) kind, well known to those skilled in the art and therefore not described in detail herein. Such devices generally include two vessels 72, 74 operated out of phase and provided with an adsorbent for the adsorption of one or other of oxygen or nitrogen from an airstream passing therethrough. In the FIG. 4 arrangement, separated oxygen and nitrogen are fed as separate streams to one or other of injection points 20, 22 and 26 and then dispensed in the manner to be described later herein. Depending on the pressure of operation, the PSA apparatus may further include a pair of compressors 76, 78 for raising the pressure of the gas before its introduction into the sidestream. These compressors may be dispensed with if injection takes place at the venturi throat.

In operation, liquor 14 is supplied to the bio-reactor vessel 12 through an inlet 12a and pump 18 is operated so as to withdraw a portion thereof outlet 12b and pass it to the sidestream 16 in which it is "treated" before being returned to the base of the bio-reactor at inlet 12c. Treatment comprises the step of introducing an oxygen rich and a nitrogen rich gas in a manner which forms discrete and separate oxygen and nitrogen rich gas bubbles of between 0.005 mm and 1.0 mm, preferably between 0.025 and 0.5 mm, most preferably about 0.2 mm, in diameter before returning the liquor to the bio-reactor. It has been found that, in many applications, the fine bubbles of oxygen and nitrogen-rich gas tend not to coalesce to any great extent and, therefore, the two gas streams can be introduced in close proximity. Consequently, the separate gas bubbles can perform their required function more efficiently than prior art systems where coarse bubbles of air are used and, hence, considerable savings can be achieved.

The point at which the oxygen and nitrogen are injected may be varied. The nitrogen-rich gas injection point 26 employs valve $V_3$ and must inject the nitrogen rich gas at a pressure greater than that created by pump 18. The oxygen injection point may be upstream of the venturi device 30 or at the throat thereof. If an upstream position is employed, valve $V_1$ is utilized to control the oxygen flow. $V_2$ is employed to control any oxygen supplied to the throat of the venturi itself. The advantage of upstream $O_2$ injection resides in the fact that the low pressure venturi throat may be used to inject air and thereby reduce the (normal) air compressor power and cost requirement. Injection at the venturi throat requires less supply pressure due to the suction effect created in the venturi itself. The requirement for a compressor might therefore be eliminated and one might employ an oxygen supply directly from a PSA apparatus as shown in FIG. 4 but without compressor 78. While it is desirable to maintain a slight separation between the oxygen and nitrogen injection points, it has been found that they may be injected at substantially the same point without significantly affecting the efficient operation of the process. One example of such an arrangement is shown in dotted lines in FIGS. 1, 2 and 4 in which additional valve $V_4$ and supply pipe 80 are employed to allow or inhibit the flow of nitrogen to the throat of venturi 30.

Once created and introduced into the sidestream, the small oxygen and nitrogen bubbles B are injected into the bulk of the liquor in the bio-reactor where they commence treatment of the liquor itself. The nitrogen bubbles act to strip undesirable $CO_2$ from the liquor as they rise to the surface S and allow the $CO_2$ to be removed via outlet 12d and may be directed for treatment in downstream off-gas scrubber 64 (FIG. 3) before being released to atmosphere. The oxygen is added to oxygenate the liquor as is well known in the art and therefore not described herein. Dissolved oxygen monitor 51 is operably linked to controller 57 which initiates control over the oxygen supply rate so as to maintain the dissolved oxygen concentration at a desired level. pH control is achieved by employing pH monitor 52 and the analytical controller 54 such as to initiate control over the flow of nitrogen rich gas as and when desired so as to maintain the pH within desired limits.

As is well known, stripping of $CO_2$ is a mass transfer process that will approach equilibrium given infinitely long contact time between the $CO_2$ stripping gas (nitrogen) bubble and the bio-reactor liquor. From experimental testing of the coarse bubble diffuser arrangements presently utilized, it has been found that such systems achieve just 23% of their potential equilibrium condition. In contrast, the small bubble diffuser arrangement of the present invention is able to achieve up to 93% of the equilibrium condition; ie 93% of the theoretical $CO_2$ stripping capability is achieved. In practical terms, this means that the present invention would need only one eighth of the gas flow to achieve the same results as the prior art processes. Consequently, it will be possible to reduce significantly the quantity of stripping gas, thereby reducing the costs associated with the production thereof. In particular, the size of any downstream off-gas scrubber 64 may be reduced as one has significantly less exhaust gas to treat. Also, the size of any nitrogen rich gas production or air compressor facility can be reduced proportionally, thereby further reducing costs.

It is thought that the advantages of employing small bubbles in accordance with the present invention result from two factors. First, the smaller bubbles have less buoyancy and tend to remain in the bio-reactor much longer than larger bubbles, thereby increasing the time available to reach equilibrium. Second, the ratio of surface area to volume is greater for small bubbles than for larger ones and, hence, mass transfer between the liquor and the bubble is significantly improved.

The effect of reactor temperature on the efficiency of $CO_2$ stripping can be demonstrated. For example, for a given organic load and a reactor temperature of 25° C., the quantity of nitrogen injected into the sidestream which would be required to control the pH to a desired value may be 100 kg/hr. At a reactor temperature of 35° the quantity of nitrogen injected to achieve the same pH value would be only 50 kg/hr. The reason that $CO_2$ stripping is more effective at high temperatures is that the solubility of $CO_2$ decreases with increasing temperature and the $CO_2$ is more effectively 'boiled' out of solution.

The fact that $CO_2$ stripping is so extremely sensitive to bio-reactor temperature is exploited by the present invention. In particular, heating of the liquor is achieved by passing hot fluid through heat exchanger 58 or 'load-managing' a number of bio-reactors so as to promote the desired temperature within at least one reactor. Steam heating of the bio-reactors using low-grade heat at 40° C. to 50° C. would also be technically possible if it were practically feasible to supply heat at this temperature to the reactors. Such low-grade heat is often available in the chemical type industries where such treatment processes may be employed.

I claim:

1. A process for the removal of carbon dioxide from liquor in a vessel comprising continuously withdrawing a portion of the liquor into a sidestream, introducing a nitrogen-rich gas into the sidestream in a manner which forms separate and discrete bubbles of between 0.005 mm and 1.0 mm diameter and returning said portion of liquor to the vessel wherein the nitrogen acts to adsorb carbon dioxide from the liquor and is then expelled from the liquor as an off-gas.

2. A process in accordance with claim 1, wherein the sidestream is returned at or near the bottom of the vessel.

3. A process in accordance with claim 1, wherein the bubbles of nitrogen-enriched gas introduced into the sidestream have a diameter between 0.025 and 0.5 mm.

4. A process in accordance with claim 1, wherein the bubbles of nitrogen-enriched gas introduced into the sidestream have a diameter of about 0.2 mm.

5. A process in accordance with claim 1, including the further step of dissolving a gas into the liquor in which the gas to be dissolved is introduced into the sidestream in a manner which forms discrete and separate bubbles of between 0.005 mm and 1.0 mm diameter.

6. A process in accordance with claim 5, wherein the gas to be dissolved in the liquor comprises an oxygen-rich gas.

7. A process in accordance with claim 6, wherein the bubbles of oxygen-enriched gas introduced into the sidestream have a diameter between 0.025 and 0.5 mm.

8. A process in accordance with claim 6, wherein the bubbles of oxygen-enriched gas introduced into the sidestream have a diameter of about 0.2 mm.

9. A process in accordance with claim 6, wherein the oxygen-rich gas comprises substantially pure oxygen.

10. A process in accordance with claim 6 including the step of monitoring the dissolved oxygen concentration in the liquor and adjusting the amount of oxygen-rich gas introduced into the sidestream in accordance therewith.

11. A process in accordance with claim 5, wherein the sidestream includes a venturi having a throat and the gas to be dissolved is injected into the sidestream at the throat or upstream thereof.

12. A process in accordance with claim 1, wherein the nitrogen-rich gas comprises natural air.

13. A process in accordance with claim 1, wherein the nitrogen-rich gas comprises substantially pure nitrogen.

14. A process in accordance with claim 1 including the step of monitoring the pH of the liquor and adjusting the amount of nitrogen-rich gas introduced into the sidestream in accordance therewith.

15. A process in accordance with claim 1 including the step of heating the liquor within the bio-reactor so as to maintain the liquor within a desired operating temperature.

16. A process in accordance with claim 1, wherein the sidestream includes a venturi having a throat and the nitrogen-rich gas is injected into the sidestream at the throat or upstream thereof.

\* \* \* \* \*